(12) United States Patent
Heine et al.

(10) Patent No.: US 7,538,866 B2
(45) Date of Patent: May 26, 2009

(54) OPTICAL SENSOR AND METHOD FOR OPTICALLY INSPECTING SURFACES

(75) Inventors: Wolfgang Heine, Taufkirchen (DE);
Dieter Spriegel, München (DE);
Michael Stockmann, Bruckmühl (DE);
Martin Weber, Markt Schwaben (DE)

(73) Assignee: Siemens Aktiengesellschaft, Munich (DE)

( * ) Notice: Subject to any disclaimer, the term of this patent is extended or adjusted under 35 U.S.C. 154(b) by 120 days.

(21) Appl. No.: 11/789,228

(22) Filed: Apr. 24, 2007

(65) Prior Publication Data
US 2007/0252976 A1 Nov. 1, 2007

(30) Foreign Application Priority Data
Apr. 26, 2006 (DE) .................. 10 2006 019 468

(51) Int. Cl.
*G01N 21/88* (2006.01)
(52) U.S. Cl. .............. 356/237.3; 356/237.2; 356/237.1; 250/559.29
(58) Field of Classification Search ......... 356/600–624, 356/237.1–237.5; 250/234–236, 406.1–406.2, 250/458.1, 559.29; 212/212, 211, 216–219
See application file for complete search history.

(56) References Cited

U.S. PATENT DOCUMENTS

| | | | |
|---|---|---|---|
| 3,370,176 A | 2/1968 | Keiper et al. | |
| 3,743,431 A | 7/1973 | Cushing et al. | |
| 3,790,287 A | 2/1974 | Cuthbert et al. | |
| 4,441,124 A | 4/1984 | Heebner et al. | |
| 4,598,997 A * | 7/1986 | Steigmeier et al. | 356/237.5 |
| 4,999,510 A * | 3/1991 | Hayano et al. | 250/559.41 |
| 5,048,967 A * | 9/1991 | Suzuki et al. | 356/401 |
| 5,108,176 A * | 4/1992 | Malin et al. | 356/243.1 |
| 5,377,001 A * | 12/1994 | Malin et al. | 356/237.2 |
| 5,798,829 A * | 8/1998 | Vaez-Iravani | 356/237.1 |
| 6,201,601 B1 * | 3/2001 | Vaez-Iravani et al. | 356/237.4 |
| 6,271,916 B1 * | 8/2001 | Marxer et al. | 356/237.3 |
| 7,100,106 B1 * | 8/2006 | Ramaley et al. | 715/234 |
| 2002/0185610 A1 | 12/2002 | Stern | |

FOREIGN PATENT DOCUMENTS

| | | |
|---|---|---|
| DE | 41 39 094 A1 | 6/1993 |
| DE | 198 13 216 A1 | 9/1999 |
| DE | 102 10 209 A1 | 9/2003 |
| EP | 0 447 848 A2 | 9/1991 |

\* cited by examiner

*Primary Examiner*—Sang Nguyen

(57) ABSTRACT

In one aspect, an optical sensor is used to detect defects, which can appear on smooth surfaces, is provided. The sensor includes a telecentric laser scanner and a detection unit. The scanner includes a laser for the approximately perpendicular illumination of a smooth surface, a scanning mirror, and a telecentric optical system for guiding illumination and detection beams the detection unit includes an optical detector system, a central diaphragm, which is concentrically positioned in the vicinity of the optical detector system in the direction toward the telecentric laser scanner, a highly sensitive photomultiplier for detecting scattered light, which emanates from defects on smooth surfaces, and a slit diaphragm arranged upstream of the photomultiplier.

16 Claims, 1 Drawing Sheet

OPTICAL SENSOR AND METHOD FOR OPTICALLY INSPECTING SURFACES

CROSS REFERENCE TO RELATED APPLICATIONS

This application claims priority of German application No. 102006019468.3 DE filed Apr. 26, 2006, which is incorporated by reference herein in its entirety.

FIELD OF INVENTION

The invention relates to a method and an arrangement for detecting defects on smooth surfaces, with defects that exhibit dimensions in the range of less than 1 μm being treated.

BACKGROUND OF INVENTION

Monitors or televisions having cathode ray tubes are being increasingly squeezed out of the market by flat screens. The flat glass used for flat screens of this type must correspond to particular standards and must, in particular, be defect free, it being possible for both surface sides of a flat glass panel to be viewed. In this way, the glass side, which is provided with electrical terminals and can thus be processed photolithographically, is to be inspected against different standards to the side of the flat glass panel pointing outwards. All in all, a complete examination of the production of a thin flat glass is necessary, since extremely small defects also influence the processing of the glass surface and can thus inhibit the function of the monitor. During the production of flat glass, a high throughput is available as standard, so that inspection or examination systems have to test this large quantity of flat glass, with the corresponding inspection covering the entire surface. The most frequent defects are punctiform or linear. As defects are also to be excluded in the submicrometer range, these must be detected and localized by means of corresponding inspection methods.

SUMMARY OF INVENTION

In order to identify punctiform, linear and laminar defects, line scan cameras provided with suitable lighting are mostly used. The defects which can be identified with this technology lie in the range of a few micrometers. Defects in the submicrometer range such as extremely small scratches for instance with a depth of a few nanometers can currently only be visually detected by expert personal using bright lights. This method can however not be used for a one hundred percent examination of the flat glass in the production cycle.

An object underlying the invention is to provide a device and a method, by means of which the complete optical inspection of smooth surfaces in respect of punctiform, linear or laminar defects is possible, with their dimensions lying in the submicrometer range. The solution of this object appears by means of the feature combination of the independent claims. Advantageous embodiments can be inferred from the dependent claims.

The concept underlying the invention such that a one hundred percent inspection of smooth surfaces, in particular of flat glass, for defects which can be punctiform, flat or laminar and the dimensions of which lie in the submicrometer range, is enabled by the use of a telecentric laser scanner in combination with a photomultiplier to detect the laser light scattered onto the defects. A very high detection sensitivity of the photomultiplier allows defects in the submicrometer range to be detected while maintaining a high data rate. In this way, a complete final inspection of smooth surfaces and/or flat glass is possible. Both the scanning illumination beam and also the detection beam path are arranged telecentrically. This allows the scattered light emanating from a defect to be captured by way of an aperture which is rotationally symmetrical to the illumination direction, which is identical to the measurement direction, as a result of which particularly fine scratches are identified over the surface irrespective of their positions on a surface in consideration of the same sensitivity. The optical construction of the sensor is very simple, since the resolution of the sensor is only determined by the focal diameter of the scanning beam. For this reason, the imaging quality of the optical scanning system must only be adjusted to the aperture of the scanning beam which is minimal in comparison with the detection beam path. The back scattered light is collected by way of an optical detection system, and the imaging quality of the optical detection system is not subject to any particular standards.

It is particularly advantageous, for the identification of scratches, to design the aperture of an optical detector system in a rotationally symmetrical manner to the optical axis. As a considerable portion of illumination light is reflected in a mirror-like manner to the surface to be inspected as a result of the telecentric design of the sensor for the illumination and also for the detection beam guide, a central diaphragm must be used to prevent the light portions of this type from reaching the photomultiplier. This can either be carried out by a diaphragm or by a tilted mirror, which is required in one variant of the sensor, by supplying and/or injecting the scanning light beam from outside into the telecentric radiation beam.

A diaphragm of this type in the center of the optical detector system blocks the light reflected in a mirror-like manner by a glass specimen surface for instance, said light being passed back onto the illumination path by virtue of the telecentric illumination. The size of the diaphragm provided here enables a certain angular tolerance of the glass specimen to the vertical illumination direction. An annular design, in other words a design of the detector aperture which is rotationally symmetrical to the optical axis, is realized by the central diaphragm irrespective of the position of the scanning beam. The advantage of this annular aperture simultaneously enables a uniform detection sensitivity for linear defects irrespective of their direction on the measurement surface.

If the detection aperture cannot be designed to be annular, but consists for instance of two opposite circular segments, an angular gap appearing in the detection region can be advantageously bridged using additional sensors, with the scanning lines of the sensors used each having to be inclined toward one another.

A described sensor can be advantageously used for the inspection of flat glass panels, with flat glass panels being able to comprise for instance a material thickness in the range of tenths of millimeters and being able to be up to several square meters in size. On the one hand, a complete inspection of the flat glass is enabled following its production. Furthermore, punctiform, laminar or linear defects can be detected in the submicrometer range. With one variant of this sensor, the depth of field of which is clearly less than the thickness of the glass to be examined, it is also possible to detect whether a defect is positioned on the upper side or on the underside of the flat glass illuminated during the measurement.

A high data rate must be available in the sensor in order to adapt to the feed rates available during the production of flat glass, so that the inspection can proceed at the same time as and/or just as quickly as the production rate. This is enabled by the use of a highly sensitive photomultiplier.

BRIEF DESCRIPTION OF THE DRAWINGS

Exemplary embodiments are described below with reference to schematic figures which do not restrict the invention.

DETAILED DESCRIPTION OF INVENTION

Figure 1:
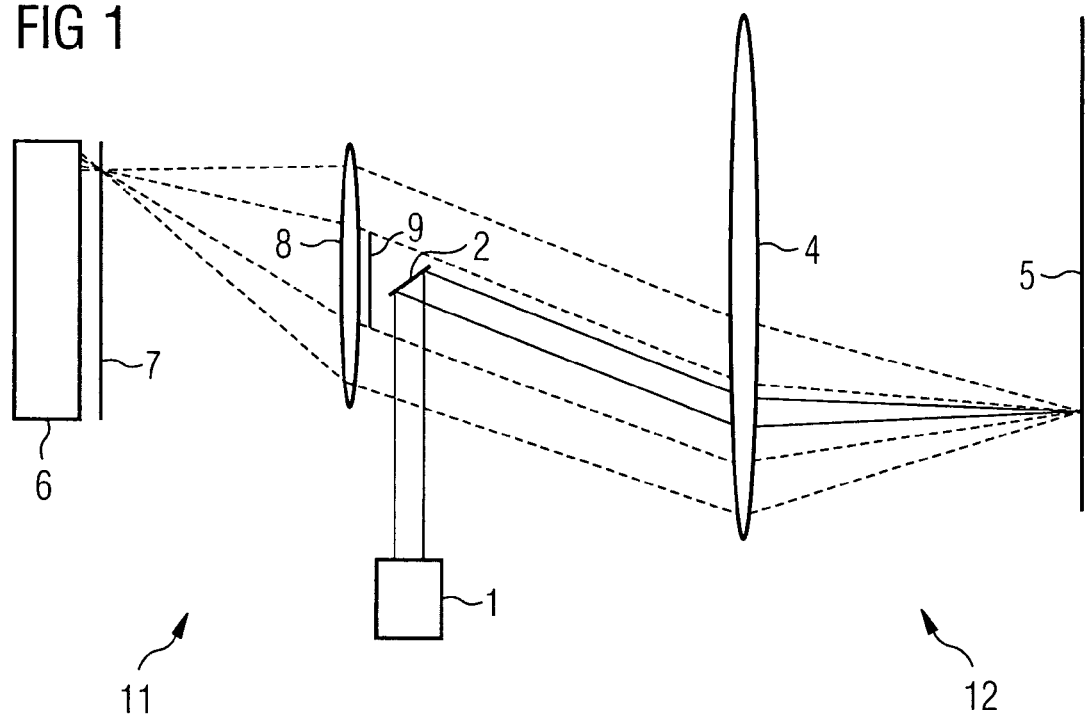
FIG. 1 shows the main design of a sensor comprising a detection unit and a telecentric laser scanner.

FIG. 1, which reproduces the main design of a described sensor, shows that the collimated light of a laser is deflected from a scanner in a specific angular range. A laser 1 generates a laser beam, which is deflected by means of a scanning mirror 2. A telecentric optical scanning system 4 focuses the deflected light onto the smooth surface 5 to be examined or onto a glass specimen. The light beams hit the surface perpendicularly, and as a result of the deflection of the scanning mirror, the laser focus on the surface describes a line. The laminar scanning of the glass specimen is achieved by the infeed of the specimen perpendicular to the scanning line. The scattered light reflected by the glass surface is collimated by the telecentric optical scanning system 4 and is focused onto a slit diaphragm 7 using a downstream optical detector system 8. The focused light flows through the slit diaphragm 7 and hits the receiving surface of a photomultiplier 6. The slit diaphragm 7 arranged upstream of the photomultiplier 6 shields this considerably from outside light, which does not emanate from the site of the laser focus on the glass surface. The diaphragm 9 in the center of the optical detector system blocks the light reflected in a mirror-like manner from the glass surface, which, by virtue of the telecentric illumination, flows back on the detection beam path, shown left in FIG. 1.

With the size of the central diaphragm 9, which can to a certain extent be of a variable design, a certain independency of the sensor compared with angular deviations is produced, so that the surface to be examined can to a certain extent be inclined toward the vertical illumination direction. The central diaphragm of the optical detector system effects an annular detector aperture irrespective of the site of the scanning beam. This annular aperture enables a uniform detection sensitivity for linear defects, irrespective of their direction on the surface to be examined.

Figure 2:
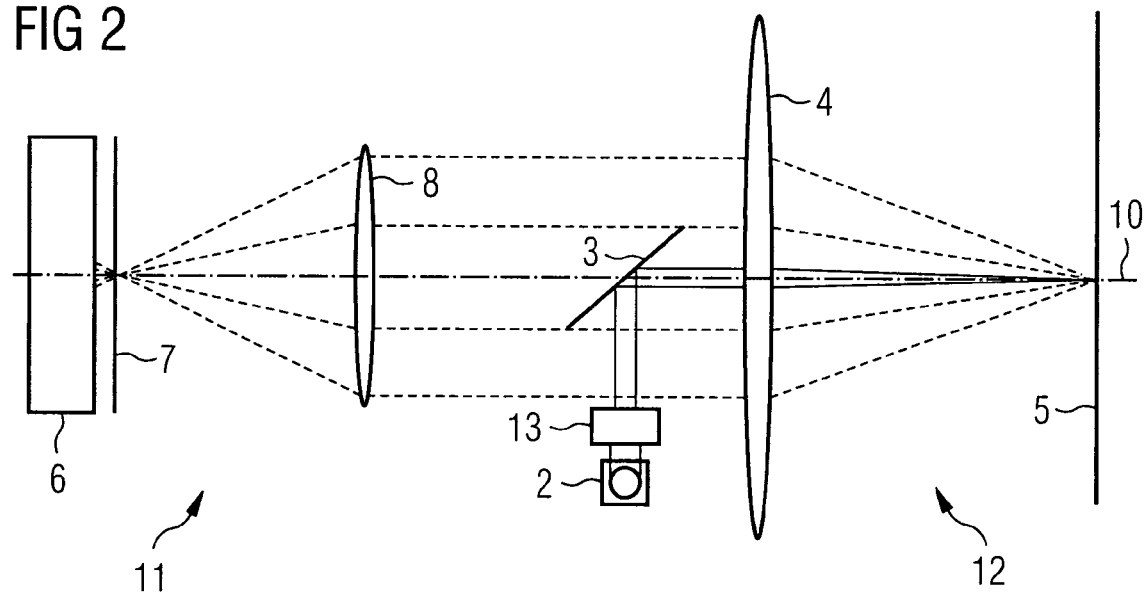
FIG. 2 shows a variant of a sensor according to FIG. 1, with a diagram rotated about 90° about the optical axis of the lens being selected.

FIG. 2 shows a variant of the diagram in FIG. 1, with an arrangement rotated about 90° about the optical axis of the lenses being selected. The optical scanning system 4 consists in this example of a further optical system, in order for instance to increase the scanning angle. As this optical component is not to be radiated from the reflected scattered light, it must be arranged outside the detection beam path. It is consequently supplied by way of a tilted mirror 3. At the same time, this tilted mirror replaces the central diaphragm 9, which can be seen in FIG. 1. In this way, the tilted mirror 3 is significantly wider than the central diaphragm 9. The detection aperture is consequently no longer annular in this example, but instead consists of two opposite circular segments. The rotation symmetry of the aperture thus lapsed results in the linear defects being clearly recognizable in all circumstances. This angular gap in the detection region can be covered by a further sensor, the scanning line of which is rotated compared with that of the first sensor such that its detection region covers the angular gap of the first sensor.

A complete examination of flat glass is thus possible, and defects, which are punctiform, laminar or linear, can be recognized and localized in the submicrometer range. In particular, the complete inspection of the surface with a rough localization of the defects is carried out using a first sensor with high depth of field and the decision as to on which side of a flat glass panel the defect lies is made using a second sensor with lower depth of field.

With a corresponding infeed of a flat glass panel, a laminar scanning of the object and thus the detection of different types of defects is achieved using the oscillating movement of the laser beam.

Fine scratches scatter the illuminating light only perpendicularly to its longitudinal axis. They are thus only visible if they are viewed perpendicularly to their longitudinal axis. To ensure that scratches of this type can be identified irrespective of their position on the glass, the aperture of the optical receiver system must be arranged rotationally-symmetrical to the illumination direction. If the aperture is not completely rotationally symmetrical for technical reasons, several sensors with overlapping aperture ranges can be used. In this way, an object surface is scanned in succession. The high measurement speed is achieved by the parallel use of several sensors. Furthermore, this illustrated modular design enables the inspection system to be adapted to glass plates of different widths.

As the depth of field of the above-described sensor is greater than the glass thickness, defects on the front and rear sides can at first not be distinguished from one another. To this end, a second sensor is provided, the depth of field of which is smaller than the glass thickness and can thus emit distance and/or height values. In practice, a complete examination is not possible using only a second sensor of this type. This is thus only used if the lateral position of a defect, which is already found using the first sensor, is fixed and thus only the height position is still to be determined.

The invention claimed is:

1. An optical sensor for detecting punctiform, linear or laminar defects on smooth surfaces, comprising:
   a telecentric laser scanner having:
      a laser for the approximately perpendicular illumination of a smooth surface,
      a scanning mirror, and
      a telecentric optical system for guiding illumination and detection beams; and
   a detection unit having:
      an optical detector system,
      a central diaphragm positioned concentrically in the vicinity of the optical detector system toward the telecentric laser scanner,
      a highly sensitive photomultiplier for detecting scattered light, which emanates from defects on smooth surfaces, and
      a slit diaphragm arranged upstream of the photomultiplier,
         wherein in the case of an incomplete rotationally-symmetrical configuration of the optical detection system, a second sensor is provided with an aperture range overlapping the first sensor, the scanning line of which forms an angle to the scanning line of the first sensor.

2. The optical sensor system as claimed in claim 1, wherein an aperture of an optical receiver system is arranged in a rotationally symmetrical manner to the illumination direction.

3. The optical sensor system as claimed in claim 2, wherein an aperture of an optical receiver system is designed to be annular.

4. The optical sensor system as claimed in claim 1, wherein an optical scanning system is arranged outside the detection beam path in order to increase a scanning angle, and the scanning laser beam is injected by way of a tilted mirror, which simultaneously represents the central diaphragm.

5. The optical sensor system as claimed in claim 1, wherein the smooth surface to be scanned by the sensor is a flat glass panel.

6. A method for detecting punctiform, linear or laminar defects on a smooth surface, comprising:
   providing an telecentric laser scanner having:
      a laser for the approximately perpendicular illumination of a smooth surface,
      a scanning mirror, and
      a telecentric optical system for guiding illumination and detection beams and
   a detection unit having
      an optical detector system,
         a central diaphragm, which is positioned concentrically in the vicinity of the optical detector system toward the telecentric laser scanner,
         a highly sensitive photomultiplier for detecting scattered light,
      which emanates from defects on smooth surfaces, and
         a slit diaphragm arranged upstream of the photomultiplier;
   illuminating a smooth surface of an object approximately perpendicularly via the telecentric laser scanner for the examination thereof;
   guiding scattered light emanating from a defect point to the highly sensitive photomultiplier for optical/electronic conversion;
   arranging the slit diaphragm upstream of the photomultiplier for eliminating outside light, on which the slit diaphragm the scattered light emanating from a defect point is focused and is conveyed further from here, before hitting the photomultiplier; and
   arranging a central diaphragm in the detection beam path to shield light reflected in a mirror-like manner by virtue of the telecentric design,
   wherein an annular aperture of the optical detector system with a uniform detection sensitivity results irrespective of the direction of the defect on the surface.

7. The method as claimed in claim 6, wherein smooth surfaces are measured on both sides from one side on a transparent material.

8. The method as claimed in claim 7, wherein the transparent material to be measured is flat glass.

9. The method as claimed in claim 6, wherein a first and a second sensor each having illumination beams with a focus diameter, the first and second sensor having a different focus diameters, so that a depth of field results in each instance, with which a complete surface-related detection of defects on both sides of the surface is possible, and the position of defects previously detected using the first sensor can be distinguished in respect of the front and rear sides of the surface.

10. The method as claimed in claim 6, wherein two sensor systems with different depths of field used in a time-offset manner are provided in order to detect the totality of all defects, and in order to determine the extent of individual defects.

11. The method as claimed in claim 6, wherein a complete coverage is achieved with the inspection of the flat surface via the parallel use of a number of sensors or sensor combinations.

12. The method as claimed in claim 6, wherein a complete coverage is achieved with the inspection of the flat surface via the parallel use of a number of sensors and sensor combinations.

13. An optical sensor for detecting punctiform, linear or laminar defects on smooth surfaces, comprising:
   a telecentric laser scanner having:
      a laser for the approximately perpendicular illumination of a smooth surface,
      a scanning mirror, and
      a telecentric optical system for guiding illumination and detection beams; and
   a detection unit having:
      an optical detector system,
      a central diaphragm positioned concentrically in the vicinity of the optical detector system toward the telecentric laser scanner,
      a highly sensitive photomultiplier for detecting scattered light, which emanates from defects on smooth surfaces, and
      a slit diaphragm arranged upstream of the photomultiplier,
      wherein the optical sensor is designed to:
         laterally locate defects on both sides using a depth of field, which detects the two sides of a flat glass panel, and
         determine the extent of the defect and thus the side of the flat glass panel bearing the defect using a depth of field which is smaller than the material thickness of the flat glass panel.

14. The optical sensor system as claimed in claim 13, wherein an aperture of an optical receiver system is arranged in a rotationally symmetrical manner to the illumination direction.

15. The optical sensor system as claimed in claim 14, wherein an aperture of an optical receiver system is designed to be annular.

16. The optical sensor system as claimed in claim 13, wherein an optical scanning system is arranged outside the detection beam path in order to increase a scanning angle, and the scanning laser beam is injected by way of a tilted mirror, which simultaneously represents the central diaphragm.

* * * * *